(12) United States Patent
Millard et al.

(10) Patent No.: US 6,712,824 B2
(45) Date of Patent: Mar. 30, 2004

(54) APPARATUS FOR POSITIONING THE ANGLE OF A BONE CUTTING GUIDE

(75) Inventors: Thierry Millard, Cestas (FR); Dirk Friedrich, Tuttlingen (DE)

(73) Assignee: Aesculap AG & CO KG (DE)

( * ) Notice: Subject to any disclaimer, the term of this patent is extended or adjusted under 35 U.S.C. 154(b) by 0 days.

(21) Appl. No.: 10/178,815

(22) Filed: Jun. 24, 2002

(65) Prior Publication Data

US 2002/0198531 A1 Dec. 26, 2002

(30) Foreign Application Priority Data

Jun. 25, 2001 (FR) .......................................... 01 08318

(51) Int. Cl.⁷ .............................................. A61B 17/56
(52) U.S. Cl. .......................................... 606/87; 606/88
(58) Field of Search .............................. 606/79, 82, 86, 606/87, 88, 102

(56) References Cited

U.S. PATENT DOCUMENTS

| | | | | |
|---|---|---|---|---|
| 4,457,307 A | | 7/1984 | Stillwell | 128/317 |
| 4,703,751 A | * | 11/1987 | Pohl | 606/62 |
| 4,759,350 A | * | 7/1988 | Dunn et al. | 606/82 |
| 5,486,178 A | * | 1/1996 | Hodge | 606/82 |
| 5,624,444 A | * | 4/1997 | Wixon et al. | 606/88 |
| 5,676,668 A | * | 10/1997 | McCue et al. | 606/87 |
| 6,033,410 A | | 3/2000 | McLean et al. | 606/88 |
| 2002/0133163 A1 | * | 9/2002 | Axelson et al. | 606/88 |
| 2003/0069585 A1 | * | 4/2003 | Axelson et al. | 606/88 |

FOREIGN PATENT DOCUMENTS

| | | | |
|---|---|---|---|
| DE | 297 04 393 | 8/1997 | ........... A61B/17/34 |
| FR | 2 718 010 | 10/1995 | ........... A61B/17/14 |
| FR | 2 776 176 | 9/1999 | ........... A61B/17/56 |

* cited by examiner

Primary Examiner—Pedro Philogene
Assistant Examiner—David A Bonderer
(74) Attorney, Agent, or Firm—Renner, Kenner, Greive, Bobak, Taylor & Weber

(57) ABSTRACT

An apparatus for positioning the cutting angle of a bone cutting guide, wherein the bone is preferably a tibia and/or a femur, which includes a first fastener to fasten the positioning apparatus to the bone such that the whole of the apparatus and the fastener of the cutting guide can rotate relative to the fastening axis, and a second fastener to fasten the positioning apparatus at a second fastening location onto the bone different from the first fastening location, so as to fix apparatus at a required position within the rotation relative to the first fastening axis.

8 Claims, 2 Drawing Sheets

APPARATUS FOR POSITIONING THE ANGLE OF A BONE CUTTING GUIDE

TECHNICAL FIELD

The present invention relates to an apparatus for positioning a cutting guide in order to cut or re-cut a bone, notably a tibia and/or a femur to which a knee prosthetic shall be applied.

BACKGROUND ART

An apparatus for positioning a cutting guide of the above type is known from the prior art, notably from French patent application No. 98 03421 (FR 2776 176 AFSA29) dated Mar. 20, 1998 by the present applicant. The prior art positioning apparatus disclosed therein features numerous disadvantages.

Firstly, the apparatus is particularly cumbersome when cutting a tibia, as it includes a main stem and fixating means located at the bottom of a tibia.

Secondly, this positioning apparatus is not universal, e.g. an identical apparatus for positioning a cutting guide is not suitable for both a tibia cutting guide and a femur cutting guide. As can be ascertained in the prior art cited above, the apparatus for positioning the tibia cutting guide is very different from the equivalent apparatus for a femur. Consequently, manufacturers of apparatuses of this type require two distinct manufacturing lines for said two positioning apparatuses surgeons also require both positioning apparatuses at hand, which is a disadvantage.

An apparatus is described in document FR-2.776.176 which includes first adjusting means for adjusting the orientation of the cutting angle relative to a second axis perpendicular to the first anchoring axis, but which does not includes second adjusting means to adjust the height of the cutting guide relative to the positioning system along the third perpindicular axis, wherein said height is constant because brackets 83 do not slide. Moreover, this system may only be used on a femur and cannot be adapted to a tibia.

According to the present invention, an apparatus for positioning a cutting guide is provided which overcomes the prior art disadvantages detailed above and which is universal, i.e. which may be used to position a tibia cutting guide as well as a femur cutting guide, and which is much less cumbersome than the known prior art apparatuses. Moreover, the apparatus according to the invention is particulary well suited ti CAMSP (computer-assisted medical-surgical procedure) techniques.

DISCLOSURE OF THE INVENTION

According to the present invention, the apparatus for positioning the cutting angle of a bone cutting guide, notably a tibia and/or femur cutting guide, includes first fastening means to fasten the positioning apparatus to the bone such that both the apparatus and the cutting guide may rotate relative to the fastening axis;

second fastening means to fasten the positioning apparatus to said bone at a second location different from the first fastening location, to fasten said apparatus at a desired location within said rotation relative to said first fastening axis;

first adjusting means for adjusting the orientation of the cutting angle rotating relative to a second axis perpendicular to first fastening axes, notably the orientation known as the antero-posterior slope; and second adjusting means to adjust the height of the cutting guide relative to the positioning apparatus along a third axis perpendicular to said fastening axis and second axis.

According to a particularly simple embodiment of reduced proportions, said first fastening means comprises a bore implemented in the body of said positioning apparatus and a screw or broach or similar to be screwed or inserted within said bore so as to fasten to the bone. Said second fastening means comprise a second bore parallel to said first bore and a second screw or broach or similar to be screwed or inserted within said second bore to fasten to the bone.

According to a preferred embodiment of the present invention, said first adjusting means includes two brackets mounted perpendicularly to the fastening axis, wherein said two brackets are linked to the fastening means of the cutting guide and are linked to one another by a transversal bracket perpendicular to said brackets and also perpendicular to said fastening axes. Said first adjusting means also includes a screw actionable by means of a knob, which acts upon the transversal bracket so as to displace it relative to the body of the positioning apparatus following the direction of said fastening axes.

This adjusting system is relatively simple because the adjustment is performed by means of simply translating said transversal bracket. However, said translation is performed relative to the fixed body which includes a plurality of contact points located onto the bone, namely a contact point fixed relative to the bone, e.g. said fastening locations, and another contact point, e.g. a portion of the area of contact of said cutting guide with said bone. Said translation is therefore transformed into a rotation of said cutting angle within a reduced rotation angle such that the antero-posterior cutting angle is best adjusted, i.e. the cutting angle along the sagittal plane for instance. A simple apparatus is therefore obtained to adjust the knee's antero-posterior slope contrary to particularly complicated apparatuses of the prior art.

According to another preferred embodiment of the present invention, said two vertical brackets slide relative to the main body within said third direction as a knob is acted upon, such that the height of the cutting guide to which they are attached by means of said fixating means can be adjusted relative to the body of said cutting guide and thus relative to the bone to which said cutting guide is fastened to.

According to yet another preferred embodiment of the present invention, further precision adjusting means are implemented in order to precisely adjust said rotation angle relative to said first fastening axis. Said precision adjusting means result from mounting said second bore onto a knob-operable stem, rendering said bore slideably mobile relative to the main body of the apparatus.

As first and second fixating screws are fastened into the bone to define an angle known as the varus/valgus angle with a certain amount of precision, said positioning can thus be refined by acting upon said knob, whereby said second fastening axis translates slightly relative to the body of the positioning apparatus. The varus/valgus angle can thus be slightly modified by acting upon the fastening configurations of the positioning apparatus by an angle comprised within plus or minus 3°, without however gravely deteriorating the bone. It is therefore a particularly simple structure of the apparatus.

According to still another preferred embodiment of the present invention, the cutting guide or the positioning apparatus thereof include a sensor to position the cutting angle within a space, notably within a system known as CAMSP, for instance as described in German utility patent No 297 04 393.5 dated Mar. 11, 1997 in the name of Aesculap AG.

According to another preferred embodiment of the present invention, the apparatus includes fastening means which may be removed from said cutting guide, wherein said fastening means comprises clasping pegs that may be clasped within respective appropriate lodgings implemented within the cutting guides.

The present invention also relates to the use of a positioning apparatus according to the invention, whether for a tibia or a femur.

The present invention also relates to the method of using a cutting guide including a positioning apparatus for positioning the cutting angle of a cutting guide for a bone, notably a tibia and/or a femur, including first fastening means to fasten said positioning apparatus to the bone such that the whole of the apparatus and the fastening means of the cutting guide may rotate relative to the fastening axis; and second fastening means to fasten said positioning apparatus at a second fastening location onto the bone, different from said first fastening location, such that said apparatus can be fastened in a required position within said rotation relative to said first fastening axis, comprising the steps of first fastening the cutting guide positioning apparatus at a location following a first fastening axis, when so fastened, pivoting said apparatus relative to said fastening axis into a required position, and then only fastening said positioning apparatus at a second location following a second fastening axis.

PREFERRED EMBODIMENT FOR CARRYING OUT THE INVENTION

Figure 2:
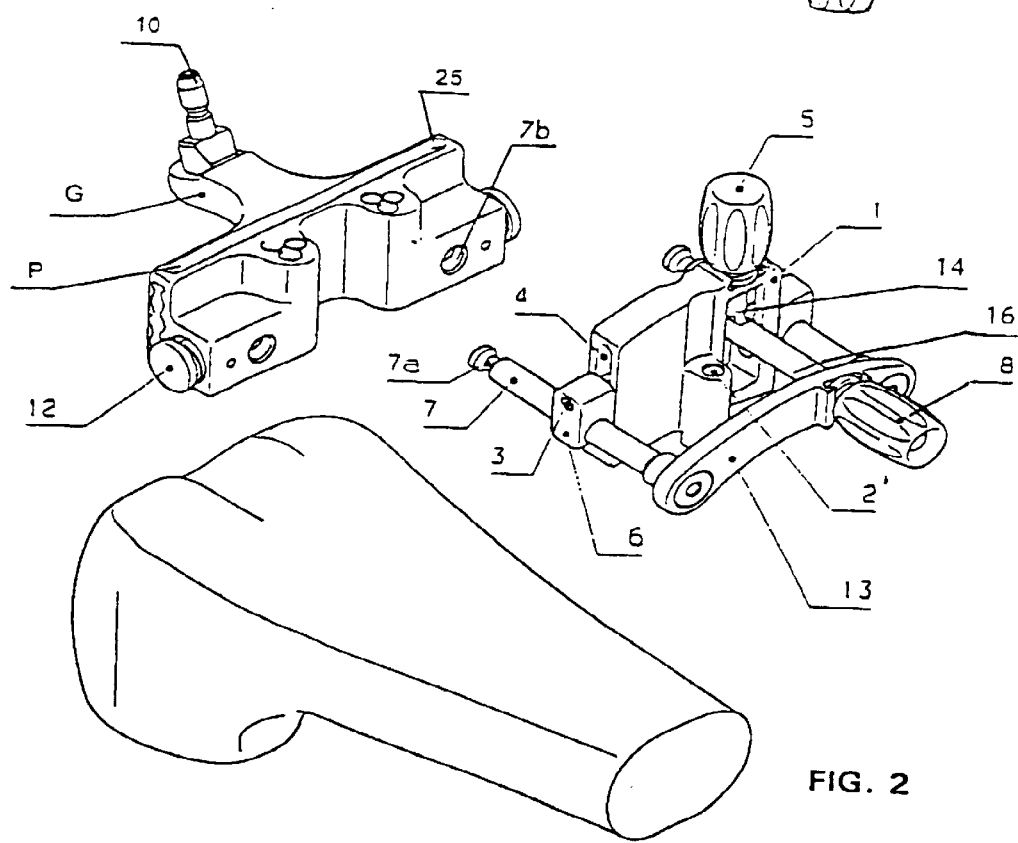
FIG. 2 is a perspective view of the positioning apparatus shown in FIG. 1 according to a different angle, featuring a right femur receiver shown at a distance, which is to be attached to said positioning apparatus and positioned relative to the femur also shown in the Figure, with a view to re-cut said shown femur in order to apply a prosthetic thereto.

An apparatus (P) for positioning a cutting guide (G) is shown in FIG. 2 which includes a basic body 1, the shape of which is preferably a hollowed out plate. The hollow 4 implemented within the base plate preferably extends over the entire width of said plate. Two raised portions jut out of plate 1. A longitudinal bore 2, 2' is implemented in each of said raised portions, each of which respectively defines a fastening axis parallel to a first direction, which will be referred to as the varus/valgus direction or fastening axes direction hereinafter.

A transversal stem 3 lodged within the hollow 4 passes through the main body 1. Two stoppers 6 are located at both extremities of transversal stem 3, which come to rest against the external edges of two opposites lateral openings of the hollow 4, such that said stem 3 may only translate within the hollow 4, wherein said translation is parallel to the direction of varus/valgus. Two vertical brackets 7 are functionally linked to said transversal stem or bracket 3 by means of said two stoppers 6, wherein said two vertical brackets 7 may slide within two bores implemented within both stoppers 6 in a direction both perpendicular to the axis of said transversal stem and perpendicular to the direction of varus/valgus, said sliding direction being hereinafter referred to as the height direction. Each of the vertical brackets 7 respectively includes a clasping peg 7a to be lodged within a respective lodging 7b implemented within the cutting guide (G), wherein said lodging is implemented by means of a valve knob 12. A stem 14 is functionally linked to said vertical stem 3. The extremity of said stem 14 opposite said stem 3 is threaded such that it may move (by means of a screwing or unscrewing action) in the direction of the fastening axis by means of a knob 5. The translation movement of the transversal stem 3 is thus controlled along the fastening axis by operating knob 5 as said stem 14 is functionally linked to said transversal stem 3.

Figure 1:
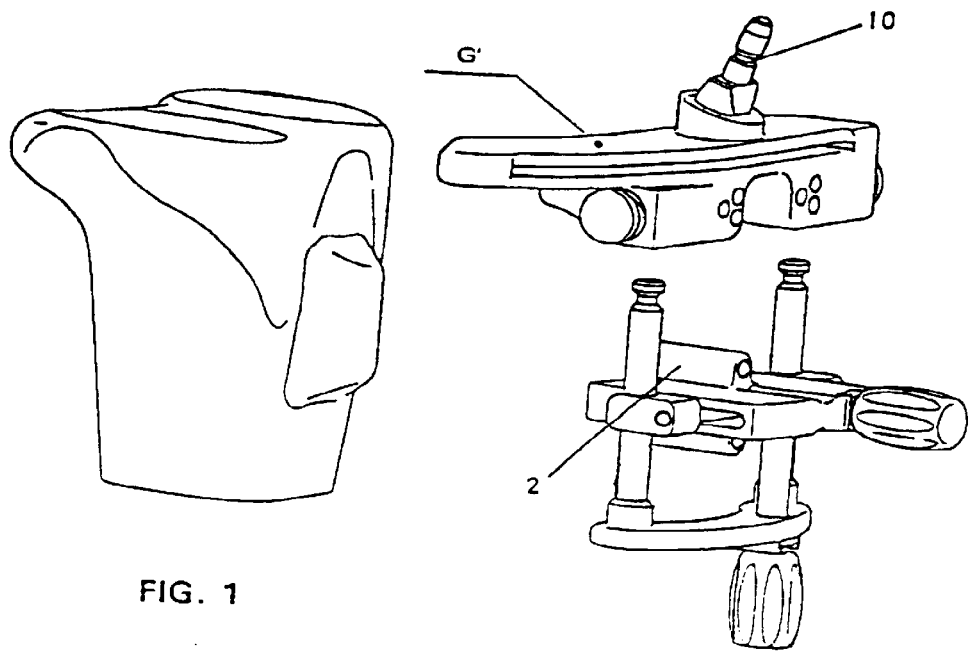
FIG. 1 is a perspective view of a first preferred embodiment of the apparatus according to the invention.
Figure 4:
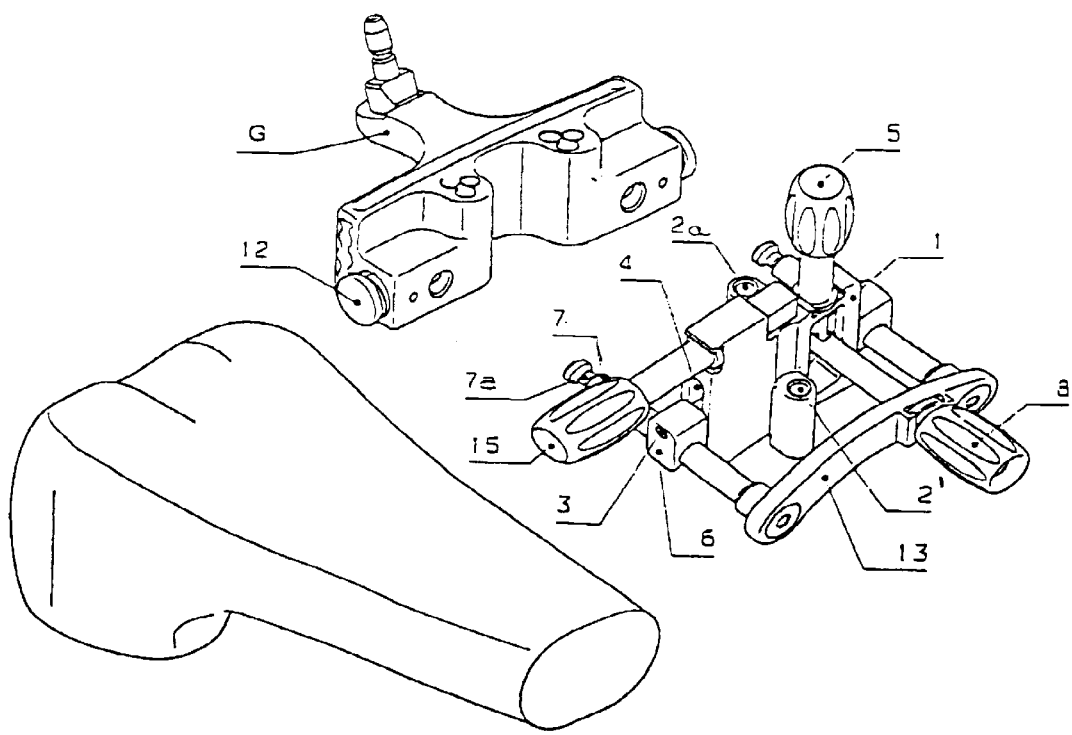
FIG. 4 is identical to FIG. 2 but relates to the second embodiment shown in FIG. 3.

Both lower extremities of said vertical brackets 7 are liked to one another by means of a base 13. A stem 16, which is parallel to brackets 7 and an extremity of which is at least partially threaded, goes through said plate 13 within a tapped hole, such that said stem 16 may move therein by being screwed or unscrewed via a knob 8. Thus the distance between the main body 1 and plate 13 can be adjusted and the extent to which the vertical bracket 7 externally jut out of said main body 1 can similarly be adjusted. The cutting guide (G) shown in FIG. 2 is a cutting guide for a femur, which is also shown in FIG. 4. It is a classical cutting guide. It includes a sensor 10 for interfacing within a system known as CAMSP (Computer-Assisted Medical-Surgical Procedure). A slit 25 defines the cutting angle (P) according to which the cutting apparatus (a blade) will be guided within said slit. The cutting guide is positioned according to the following steps:

Firstly, a surgeon fastens the apparatus to a front lateral side of the tibia or femur by means of a first fastening bore 2. The surgeon thus attempts to position the apparatus as close as possible to the location where the cutting guide should be finally located. As the first fastening screw is eventually screwed or fastened to the tibia or femur, the surgeon may then rotate the positioning apparatus relative to the fastening axis to obtain the exact positioning desired for the cutting guide, e.g. the varus/valgus angle is set. The cutting angle (P') is therefore positioned within a first angle as perpendicular as possible relative to the mechanical tibia axis (passing through the centre of the articulations), e.g. inclined relative to the angle perpendicular to the longitudinal axis of the tibia as shown in FIG. 1 and which is the angle perpendicular to the anatomical axis. As said varus/valgus angle is eventually set, preferably with the assistance of the CAMSP sensor 10, the surgeon fastens the apparatus with using the second bore 2' and the second fastening screw. The whole of the apparatus cannot rotate any further and is thus fixed in so far as the varus/valgus angle of the cutting angle is concerned, when both fastening screws are fastened to the front lateral side of the tibia.

The surgeon may now set the orientation of the cutting angle within a rotation relative to the axis 12, e.g. define the antero-posterior slope to be given to the cutting angle, by means of operating knob 5. The surgeon actions said knob 5, which will thus push or pull the transversal stem 3 in a direction parallel to the fastening axis. The link between the transversal stem 3 and the vertical brackets 7 therefore causes said vertical brackets 7 to rotate relative to the main body 1. A translation movement of the transversal stem 3 results in an increased movement of the free extremities of the vertical brackets 7 and thus results in a rotation of the angle (P) relative to the axis 3. Consequently, the cutting angle will more or less incline relative to the body 1 of the positioning apparatus according to an angle defined by the rotation relative to the axis 3. The antero posterior slope angle of the cutting angle is thus defined.

As soon as the antero posterior slope and the varus/valgus angle have been defined and positioned by the surgeon, said surgeon may now finally define the height of the cutting angle relative to the fixed main body 1. Said surgeon thus actions knob 8 which will raise or lower the vertical brackets 7 by means of screwing or unscrewing the stem 16 and therefore define the height of the cutting guide (and thus of the cutting angle P) relative to the main body 1.

The whole of the above description may apply to a femur in exactly the same manner. A cutting guide G for a femur is shown in FIG. 2. As may be observed, the cutting guide (G') for a tibia is different from the cutting guide G as it is slightly curved. However, the positioning apparatus may be adapted to both types of cutting guides, and even three types as a left cutting guide is also required for the tibia. Rather than relying on his own judgement, a surgeon may also use the sensor 10, which shows the position of the cutting angle and the position of an ideal mechanical tibia angle when interfaced with various other receivers, on a screen. Therefore, a surgeon may exactly position the cutting guide angle relative to the ideal mechanical tibia axis on a screen by means of a computer such that both angles match one another and therefore ideally position the cutting guide for re-cutting a tibia or a femur.

Figure 3:
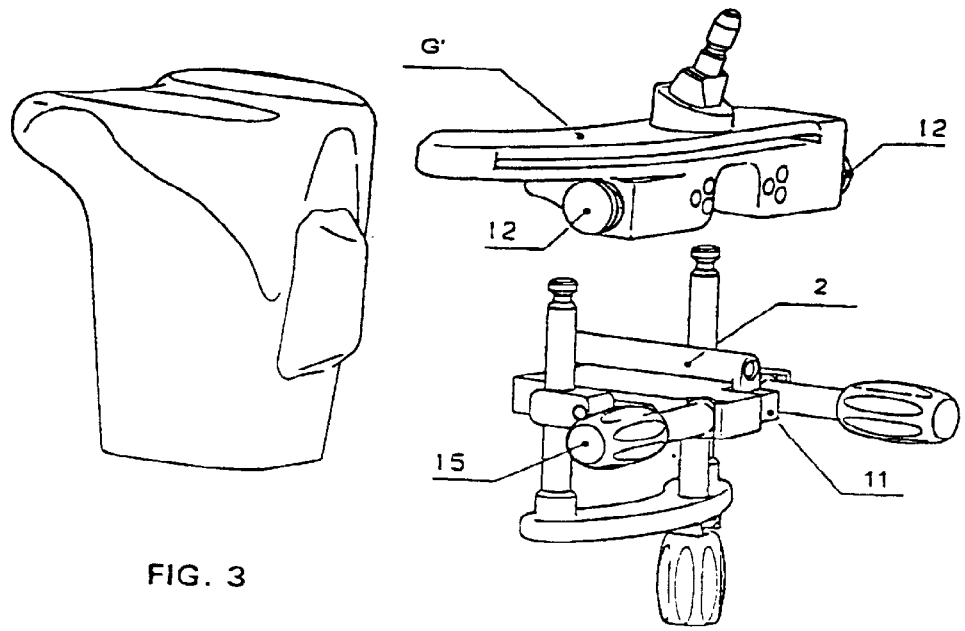
FIG. 3 is a perspective view of another preferred embodiment of the positioning apparatus shown in FIG. 1.

An alternative embodiment of the apparatus shown in FIG. 1 is shown in FIGS. 3 and 4.

The difference between both apparatus is that one of the raised portions within which bores are implemented (as 2a in FIGS. 3 and 4) is not mounted solidly onto the main body 1 of the positioning apparatus but is mounted thereon such that it may translate relative to said body by means of a manually operated stem 11, which is itself acted upon by means of screwing or unscrewing a knob 15. The position of the screw screwed within bore 2a may therefore be further adjusted relative to the body 1 in order to further adjust the varus/valgus angle, by means of the play on both fastenings, after both fastening screws have been fastened. Said further adjustment is obviously a very fine adjustment as it relies upon the slackness of the fastenings tolerance. Generally, it is not possible to further adjust the angle within a domain exceeding plus or minus three degrees, owing to the slackness of the fastenings of both screws 2a, 2'. The remainder of the apparatus is identical in all points to the description provided in relation to FIGS. 1 and 2.

What is claimed is:

1. An apparatus for positioning the cutting angle of a bone cutting guide comprising:

first fastening means to fasten said positioning apparatus to a bone such that all of said apparatus and cutting guide fastening means can rotate relative to the fastening axis;

second fastening means to fasten said positioning apparatus at a second fastening location onto said bone, different from the first fastening location, such that said apparatus is fixed in a required position within said rotation relative to said first fastening axis;

first adjusting means for adjusting the orientation of the cutting angle in rotation relative to a second axis perpendicular to said first fastening axis, wherein said orientation is known as the antero posterior slope; and second adjusting means to adjust the height of said cutting guide relative to said positioning apparatus along the third axis perpendicular to said first fastening axis and to said second axis.

2. The apparatus according to claim 1, wherein in that said first fastening means includes a first bore implemented within the body of said positioning apparatus and a screw to be screwed or introduced within said first bore in order to be fastened into said bone; and said second fastening means includes a second bore parallel to said first bore and a second screw to be screwed or introduced within said second bore so as to be fastened into said bone.

3. The apparatus according to claim 2, wherein said first adjusting means includes two brackets mounted perpendicular to said fastening axes, wherein said two brackets are linked to said fastening means of said cutting guide and are linked to one another by a transversal bracket which is perpendicular to said two brackets and also perpendicular to said fastening axis, and a stem partially threaded and actioned by a knob which acts upon said transversal bracket to move it in the direction of said fastening axis relative to the body of said positioning apparatus.

4. The apparatus according to claim 3, wherein said two vertical brackets slide in said third direction relative to said main body when a knob is actioned, whereby the height of the cutting guider to which they are fixed is adjusted by means of said fastening means relative to the body of said cutting guide and thus relative to the bone to which said cutting guide is fastened to.

5. The apparatus according to claim 1, wherein precision adjusting means are further included for precisely adjusting the rotation angle relative to said first fastening axis.

6. The apparatus according to claim 5, wherein said precision adjusting means result from said first bore being slidably mounted relative to the main body of said apparatus by means of a stem actioned by a knob.

7. The apparatus according to claim 1 wherein said cutting guide or the positioning apparatus thereof include a sensor to position said cutting angle (P) within a space, whereby said positioning takes place within a system known as CAMSP.

8. The apparatus according to claim 1, characterised in that it includes fastening means that may be removed from said cutting guide, which includes clasping pegs to be clasped within respective lodgings implemented within said cutting guides.

* * * * *